United States Patent
Matheis et al.

(10) Patent No.: US 10,610,629 B2
(45) Date of Patent: Apr. 7, 2020

(54) DEVICE WITH INLET PORTION FOR TREATING A BIOLOGICAL LIQUID

(71) Applicant: Novalung GmbH, Heilbronn (DE)

(72) Inventors: Georg Matheis, Heilbronn (DE);
Fabian Metzger, Heimsheim (DE);
Josef Bogenschutz, Bisingen (DE);
Ralf Roßbroich, Aachen (DE)

(73) Assignee: Novalung GmbH, Heilbronn (DE)

( * ) Notice: Subject to any disclaimer, the term of this patent is extended or adjusted under 35 U.S.C. 154(b) by 106 days.

(21) Appl. No.: 15/572,294

(22) PCT Filed: May 9, 2016

(86) PCT No.: PCT/EP2016/000750
§ 371 (c)(1),
(2) Date: Nov. 7, 2017

(87) PCT Pub. No.: WO2016/177476
PCT Pub. Date: Nov. 10, 2016

(65) Prior Publication Data
US 2018/0117231 A1  May 3, 2018

(30) Foreign Application Priority Data

May 7, 2015 (EP) .................................... 15001369

(51) Int. Cl.
*A61M 1/16* (2006.01)
*B01D 63/04* (2006.01)

(52) U.S. Cl.
CPC ......... *A61M 1/1698* (2013.01); *B01D 63/043* (2013.01); *A61M 2209/088* (2013.01)

(58) Field of Classification Search
CPC .... A61M 1/2698; B01D 63/043; B01D 63/04
See application file for complete search history.

(56) References Cited

U.S. PATENT DOCUMENTS

| 4,422,939 | A | * | 12/1983 | Sharp | B01D 29/21 210/445 |
|---|---|---|---|---|---|
| 5,162,101 | A | * | 11/1992 | Cosentino | A61M 1/1698 128/DIG. 3 |
| 6,117,390 | A | | 9/2000 | Corey, Jr. | |
| 2012/0190103 | A1 | | 7/2012 | Maurer | |
| 2012/0193289 | A1 | | 8/2012 | Cloutier et al. | |
| 2012/0321512 | A1 | | 12/2012 | Kawamura et al. | |
| 2013/0043177 | A1 | | 2/2013 | Taylor et al. | |

(Continued)

FOREIGN PATENT DOCUMENTS

| CN | 202459508 U | 10/2012 |
|---|---|---|
| DE | 4308850 A1 | 9/1994 |
| EP | 0376298 A1 | 7/1990 |

(Continued)

*Primary Examiner* — Ariana Zimbouski
(74) *Attorney, Agent, or Firm* — Dinsmore & Shohl LLP

(57) ABSTRACT

A device for treating a biological liquid has a housing with a first chamber defining a cavity and which is adapted to receive a liquid to be treated. At least one gas exchanger is at least partly disposed in the first chamber. An inlet portion is formed in a first surface of the housing for the inlet of the liquid to be treated into the chamber. The inlet portion is formed at an acute angle relative to the surface of the housing. Such a device allows a gas exchange in a lung assist method for example.

16 Claims, 7 Drawing Sheets

(56) References Cited

U.S. PATENT DOCUMENTS

2015/0314059 A1 11/2015 Federspiel et al.
2016/0095969 A1* 4/2016 Maurer ............... A61M 1/1698
                                                  422/48

FOREIGN PATENT DOCUMENTS

| EP | 0521495 A2 | 1/1993 |
| EP | 1864709 A2 | 12/2007 |
| GB | 1480406 A | 7/1977 |
| JP | H04193178 A | 7/1992 |
| JP | 2009509351 A | 3/2009 |
| JP | 200982695 A | 4/2009 |
| WO | 2009110652 A1 | 9/2009 |
| WO | 2009155248 A1 | 12/2009 |
| WO | 2014183852 A1 | 11/2014 |

* cited by examiner

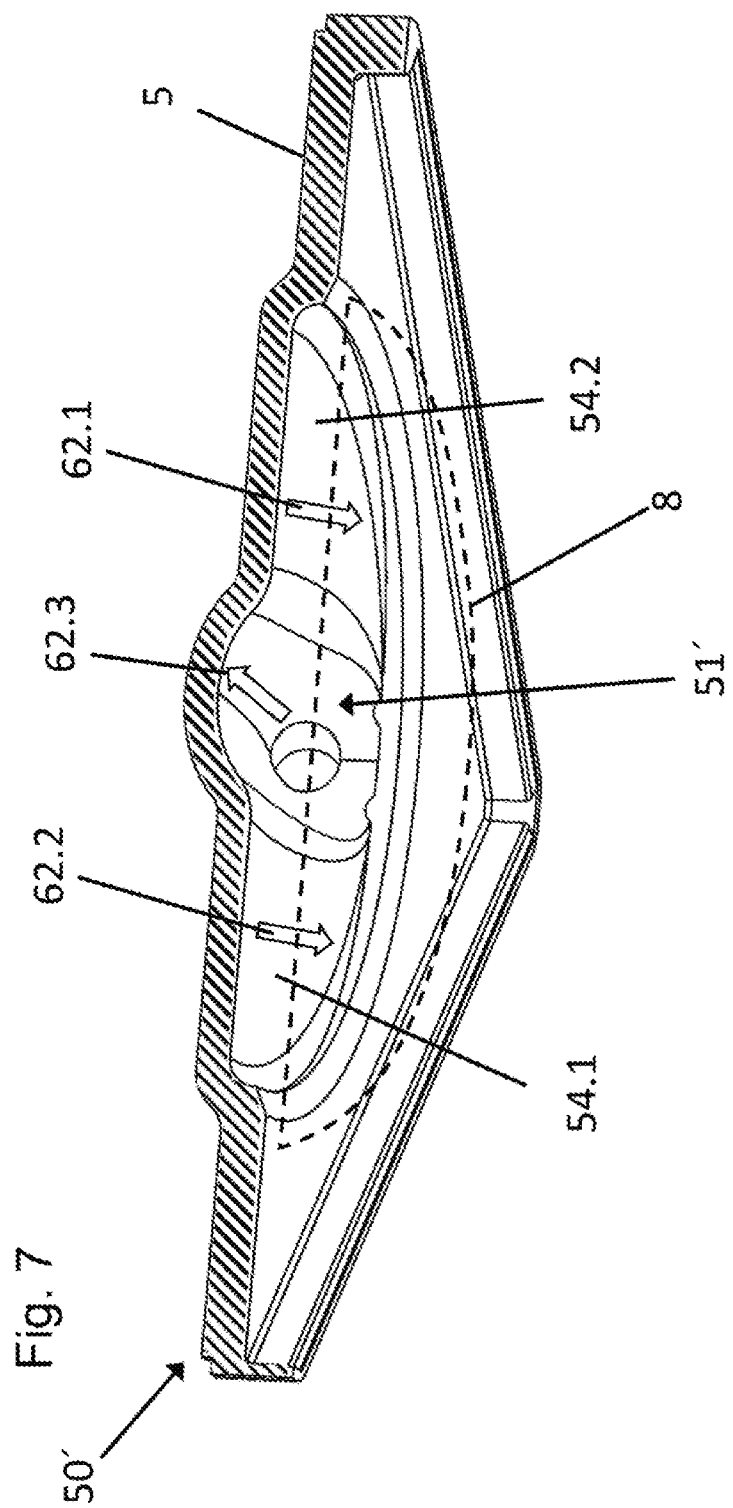

DEVICE WITH INLET PORTION FOR TREATING A BIOLOGICAL LIQUID

CROSS-REFERENCE TO RELATED APPLICATIONS

This application is the U.S. national stage of PCT/EP2016/000750 filed May 9, 2016, which claims priority of European Patent Application 15001369.6 filed May 7, 2015 of which is hereby incorporated by reference in its entirety.

FIELD OF THE INVENTION

The invention relates to a device for treating a biological liquid according to the preamble of the independent claim and, in particular, a device with a chamber, which is designed to receive the biological liquid, and with a gas exchanging means.

BACKGROUND OF THE INVENTION

This can be a gas supply or gas removal device, in which one or more gases can pass from one medium to another medium, or a gas exchanging device, which enables the exchange of one or more gases between two media. Such devices are used in chemistry, biotechnology, and medicine. An important purpose in medicine is the enrichment of a biological liquid—in particular, of blood—with oxygen and/or the removal of carbon dioxide from the liquid—especially, blood. Such measures are necessary, for example, when treating various pulmonary diseases. In addition, such measures may also be necessary, in, for example, in case of acute respiratory failure, as well as for replacing the lung when bypassing it with an extracorporeal circulation, in the mechanical support of the heart, to various degrees, and for being able to operate on a stopped heart.

Moreover, the only long-term effective therapy option for patients with end-stage functional pulmonary disease is the lung transplant. There is no other medical solution for permanently replacing the function of the lungs. For patients who suffer from chronic pulmonary diseases and are not, or not directly, being considered for a lung transplant, there is therefore a need for artificial lung assistance methods.

In order to make possible such a lung assistance method, so-called blood gas exchangers are known from the prior art.

A blood gas exchanger—often also called an oxygenator or artificial lung—is used either to completely take over the lung function short-term during open-heart surgery or to completely or partly support the lung long-term in the intensive care unit. The main function of such a blood gas exchanger consists in the supplying of oxygen to the blood (oxygenation) and in the removal of carbon dioxide from the blood (decarboxylation). The gas exchange takes place, for example, by means of hollow fiber membranes around which blood flows in an extracorporeal gas exchanger, while oxygen-rich or carbon dioxide-poor gas is conducted through the interior of the fiber at the same time. As a result of the concentration difference, oxygen or carbon dioxide can diffuse in a respectively opposite direction through a semi-permeable membrane—generally, a gas-permeable membrane. The fibers can be procured commercially and are delivered, for example, in quadrangular fiber mats or as individual fibers wound on reels.

Two different production methods exist for producing blood gas exchangers from the fiber mats—namely, wound or laid. By way of example, only a fiber mat production based upon the laid variant is to be outlined here, in order to better illustrate the background of the invention.

In the laid variant, the individual fiber mats are layered in a crisscross fashion, which results in a cuboidal—in particular, cubical—package-shaped fiber bundle. The fiber bundle is delimited toward the outside by two covers, which contain the inflow geometry, and by a casting compound. The covers are placed below and above the fiber bundle. The four sides of the fiber bundle are cast on a centrifuge, one side after the other, and connected in this way to the covers. Commercially available gas exchangers produced in this way furthermore have a corresponding cubical cavity, in which the fibers are embedded and in which blood flows around the fibers. The flow generally approaches these gas exchangers at one of the four corners of the fiber bundle or the cavity. The connections for the blood-carrying tubes are in this case oriented orthogonally to the covers of the gas exchanger.

As a result of the size and arrangement of the connections for the blood-carrying tubes, the use of these gas exchangers is, however, limited to stationary applications, in which the patient—awake or sedated—lies in bed. Since patients with chronic pulmonary diseases, who are dependent upon one of these known gas exchangers, are thus considerably limited in their mobility, not just the quality of life of the patients is significantly impaired. Modern therapy approaches, which aim for mobilization of patients, cannot be implemented either.

Known gas exchangers—in particular, gas exchangers intended for use in a heart lung machine (HLM)—are too bulky and too heavy to be carried on the body by a patient, for example. In this respect, the previously common orthogonal orientation of the tubes and connectors of such gas exchanges, which results in a large space requirement for the gas exchanger, is also an argument against such mobile use of a portable gas exchanging device.

SUMMARY OF THE INVENTION

The present invention is based upon the aim of providing an improved device for treating a biological liquid, which device eliminates at least one of the disadvantages of the known systems and provides a space-saving gas exchanger—in particular, also for a mobile application of the gas exchanger. Predominantly, it is an aim of the present invention to provide a portable gas exchanger for a patient. It is, in particular, an aim of the present invention to reduce space requirements of a gas exchanger so that transporting the gas exchanger—preferably, directly—on a patient's body is made possible.

The aim of the present invention is achieved by a device according to claim 1. Advantageous developments of the invention are the subject matter of the dependent claims.

According to one aspect of the invention, a device for treating a biological liquid is provided, which device has a housing with at least one first chamber, which forms a cavity, and a gas exchanging means that is at least partly arranged in the first chamber. The first chamber is designed to receive a liquid to be treated—here, in particular, a biological liquid, such as blood. On a surface of the housing, which is also called the inlet surface below, an inlet portion is formed for the inlet of the liquid to be treated into the first chamber. The inlet portion is in this case formed according to the invention at an acute angle relative to the inlet surface of the housing, on which the inlet portion is formed.

In particular, the device according to the invention can have a second chamber at least partly formed in the first chamber or can form a second chamber as a gas exchanging means. The second chamber is designed to receive a first fluid—in particular, a first gas. The second chamber can be formed separately from the first chamber by at least one semi-permeable membrane. The semi-permeable membrane is preferably a gas-permeable and liquid-impermeable membrane. The membrane can, for example, serve to transfer at least one predeterminable molecule type between the first and second chambers. The transfer can in this case take place from the first chamber into the second chamber and/or from the second chamber into the first chamber. In this respect, a plurality of first and/or second chambers can also be provided.

"Semi-permeable" in the context of the invention is to be understood such that the wall is partly permeable. A permeability is to be provided in this case for predetermined molecules—in particular, for specific gas molecules, such as oxygen or carbon dioxide. In this sense, the term "semi-permeable" also includes a selective permeability by specific, predeterminable molecules or compounds.

The gas exchanging means—in particular, the second chamber—can be designed and arranged such that the gas exchanging means is limited or surrounded by the at least one gas-permeable and liquid-impermeable membrane and such that a biological liquid provided in the first chamber can at least partly surround or flow around the gas exchanging means.

To the extent that a "second chamber" is referred to below, it serves only to make understanding the present invention easier. The second chamber is, however, to be understood only as a part of certain special embodiments of the gas exchanging means. In this respect, the gas exchanging means refers to all structures that make possible within the meaning of the invention a gas exchange between a liquid to be treated, e.g., a biological liquid, such as blood, and a fluid required for the gas exchange.

The membrane between the first chamber and the gas exchanging means is generally semi-permeable and normally has pores, the size of which determines the function and effect of the respective membrane. In other words, each membrane may, on the one hand, be a porous membrane, i.e., a membrane having discrete pores. On the other hand, the membrane may be a homogeneous solubility membrane without discrete pores, in which the transport of substances takes place by dissolving the permeate (e.g., the gas) in the polymer, and the separation takes place as a result of the differing solubilities in the polymer. Preferably, the membrane is a nonporous permeable membrane. In this way, a gas exchange between the fluid in the gas exchanging means and the biological liquid in the first chamber can be made possible. The exchange of gases may be subject to the convective and diffusive exchange of substances. Preferably, the exchange of gases is diffusive and is determined by the difference in the gas concentration on both sides of the membrane.

Compared to the generally orthogonal connectors used in the known stationary systems, the device according to the invention for treating a biological liquid can allow for a space-saving supply of the liquid into the first chamber by means of the angled arrangement of the inlet portion relative to the surface of the housing. According to the invention, a tangential inflow and supplying and discharging of the liquid can take place, so that the supply and discharge lines can be conducted along almost the same plane in which the housing or the housing surface is also formed. This can, in particular, allow for a transport close to or almost directly on the body—for example, the body of a patient. This can increase mobility of the device and, consequently, also of a user.

In this respect, it goes without saying that all components coming into contact with the liquid can be produced in a sterile manner or be sterilized.

The first chamber is preferably designed as a flow-through chamber and has an inlet and an outlet that is separate from the inlet. The second chamber can preferably also be designed as a flow-through chamber. The first chamber can in this case be preferably designed for flow in a direction opposite or transverse to the flow direction of the second chamber.

In some embodiments of the invention, the gas exchanging means—in particular, the second chamber—is divided into several subchambers, so that the device comprises several second chambers which are designed to receive a gas and are separated from the first chamber by a gas-permeable and liquid-impermeable membrane. The several second chambers are located inside the first chamber or are substantially surrounded by the first chamber. The second chambers preferably have an elongated and, preferably, substantially cylindrical structure, which has, in its cross-section, one or several continuous cavities. A wall, delimiting the cross-section, of the second chamber at least partly forms the gas-permeable and liquid-impermeable membrane.

In a development of the invention, the several second chambers are arranged in one or several rows next to each other, and preferably also at a distance from one another. The several second chambers can furthermore be arranged in several layers. The second chambers are, for example, designed as hollow bodies—preferably, hollow fibers—so that the wall of each hollow body or each hollow fiber forms the gas-permeable and liquid-impermeable membrane. The distance between the several second chambers arranged next to each other is preferably in the range of 50 µm to 1 cm—more preferably, in the range of 100 µm to 1 mm, and, even more preferably, in the range of 100 µm to 500 µm. This distance can be selected or adjusted arbitrarily.

In advantageous developments of the present invention, the housing furthermore has an outlet portion on a surface—the outlet surface—of the housing for the outlet of the biological liquid from the device. In this case, the outlet portion can also be arranged at an acute angle relative to the surface of the housing. The angle that the outlet portion encloses with the outlet surface can in this case be, in particular, the same angle as the one that the inlet portion encloses with the respective inlet surface. In this way, space requirement for the device can be further reduced, since a previously necessary, space-requiring orthogonal arrangement of the outlet connector, and thus a corresponding orthogonal conduct of lines, can be avoided.

It is alternatively conceivable for the angle that the outlet portion encloses to differ from the angle that the inlet portion encloses with the respective surface. Especially with respect to mobility of a carrier, this can allow for consideration of the anatomy of the carrier, or of the position of the device on the carrier or in a housing or in a carrying device. The outlet portion can basically also be provided on the same surface of the housing as the inlet portion.

It also goes without saying that the relative position of the inlet portion and the outlet portion can vary. For example, the inlet and the outlet portions can be arranged horizontally next to each other, or vertically one above the other. Both a parallel and an orthogonal arrangement of the outlet portion relative to the inlet portion are also possible. In some embodiments of the present invention, the outlet portion is located diametrically opposite the inlet portion. It is also conceivable for the inlet portion to be arranged at a position that is located, in a position in which the device according to the invention is usually used, on an upper portion of the gas exchanging device. The outlet portion can in this case be, in particular, formed on a lower portion of the device. A flow through the device from the inlet portion to the outlet portion can thereby be facilitated—in particular, because the gravitational force can support the flow of the liquid through the device. In this way, the cardiovascular system of a patient who carries the gas exchanging device can be relieved.

In some developments of the invention, the angle that the inlet portion encloses with the respective inlet surface, i.e., the inlet angle, and/or the angle that the outlet portion encloses with the outlet surface of the housing, i.e., the outlet angle, is less than 45°—preferably, less than 25°, and, in particular, between 15°-20°.

The inlet portion can be formed on the surface of the housing such that a biological liquid guided through the inlet portion can be supplied to the first chamber such that it is guided into the first chamber at a central region of the gas exchanging means—in particular, of the fiber bundle. A central region, in this respect, denotes a region of the gas exchanging means, or of the fiber bundle, which is located in a lateral extension, i.e., in the directions that substantially span a surface parallel to the inlet surface, in the center, or in the region of the center, of the fiber bundle.

It goes without saying that the supply and/or discharge line for the first fluid or additional components into the housing can take place tangentially or at an obtuse angle—for example, relative to a circumferential surface of the housing. In this way, further space savings can be made possible for the gas exchanging device.

In some embodiments, the gas exchanging means—in particular, the second chamber or the second chambers—is designed as a fiber bundle formed by a plurality of hollow fibers and arranged at least partly in the first chamber.

The first chamber can have a substantially cylindrical shape. In this way, a cavity is formed, which has a substantially cylindrical shape. This means that the cavity has no corners in the edge regions and no irregular edge regions. Additionally or alternatively, the gas exchanging means—in particular, the fiber bundle—can also have a substantially cylindrical shape. In some embodiments, the shape of the gas exchanging means or of the fiber bundle and the shape of the cavity, i.e., the inner contour of the first chamber, can have shapes and dimensions that are adapted to one another so that the gas exchanging means can be arranged as ideally as possible in the cavity of the first chamber. An ideal arrangement in this context would be an arrangement in which the biological liquid flows evenly—preferably, laminarly and with a substantially constant, even flow velocity over the entire flow cross-section—around a largest possible region of the gas exchanging means.

From the prior art are known to the person skilled in the art devices that have a gas exchanger with a cubical cavity for a biological liquid to flow through. By arranging the outlet portion and the inlet portion at an acute angle to the respective surface, a parallel, or at least approximately parallel, inflow of the second chambers can take place. The use of a cylindrical cavity in accordance with the development of the invention described above, according to some embodiments, can allow for a more homogeneous distribution of the flow velocity, compared to a cubical cavity.

The use of a cylindrical fiber bundle can, moreover, make possible a better utilization of the cavity, i.e., of the space in the first chamber available for the gas exchange. This can reduce [sic] the reliability and durability of the device—for example, by reducing occurring turbulences and resulting degenerations. Such degenerations take place, in particular, in corner regions of a cubical cavity, which results in an increased coagulation risk in the first chamber when using blood as the liquid. The formation of a cylindrical cavity reduces this risk by avoiding such corner regions. Cylindrical fiber bundles are, naturally, also basically suitable for the inflow by means of orthogonally-arranged inlet portions.

The gas exchanger can have a diaphragm seal on a side, facing the inlet portion, of the first chamber. The diaphragm seal serves to balance pressure differences in a flow cross-section of the biological liquid. The flow cross-section of the liquid in this respect denotes the entire region through which the liquid flows or which the liquid front occupies in the first chamber. Particularly when using biological liquids, such as blood, it is desirable that the liquid flow evenly through the device—in the present case, the first chamber of the device—without turbulences occurring in the flow profile.

Otherwise, regions can, in particular, form in which the flow rate is considerably reduced, such that an increased accumulation of liquid components forms on the walls—above all, also on the membranes to the gas exchanging means. This can, on the one hand, impair the function of the gas exchange. On the other hand, this can result in contamination of the liquid when the deposited material peels away from the walls again. A diaphragm seal, which can bring about a more even distribution of the inflow pressure into the first chamber, can reduce this effect. Such a diaphragm seal can thus increase the reliability of the device according to the invention.

Advantageously, the diaphragm seal can have a substantially oblique plane, along which the biological liquid is guided when flowing into the device. This can further reduce the formation of pressure differences and flow separations, i.e., stationary vortices, can be avoided better.

In some embodiments of the invention, at least one of the surfaces of the device, viz., the inlet surface and/or the outlet surface, has a cover, or, as a whole, constitutes a cover. Such a cover can in, particular, be formed as a removable cover, so that access to the first chamber or to the gas exchanging means—in particular, to the second chamber—in the device is made possible. In this case, the cover is basically arranged in a region upstream of the first or the second chamber. The cover can also be connected to the second chamber or to the second chambers, and close them to the outside.

In advantageous embodiments, a diaphragm seal can be provided at least on the cover of the inlet surface on its inner surface—preferably, in the shape of an oblique plane. In this way, a pressure difference, which is caused by the asymmetrical inflow, can already at least partly be balanced at the inlet of the liquid. In this way, a more homogeneous pressure distribution, and consequently a more homogeneous distribution of the flow velocities, can again take place. Such a diaphragm seal is also called a blood distributor plate.

In yet other developments, a distributor means can be formed in the device, which distributor means is designed to distribute the biological liquid in a direction substantially lateral to the flow direction. In this way, an improved inflow of a larger area of the gas exchanging means—in particular, of a fiber bundle or of the second or additional chambers—can be achieved. In this way, the efficiency of the device can be increased by means of as optimal an inflow as possible of the entire available surface of the gas exchanging means. As a result of increased efficiency, this can allow for further miniaturizations of the device. The distributor means can also be formed integrally with the diaphragm seal.

In advantageous developments of the invention, the distributor means has a channel-like portion starting from a side facing the inlet portion and opening in the lateral direction in the flow direction of the biological liquid. A "lateral direction" in this case represents a direction that substantially extends in the same direction as the inlet surface on which the inlet portion is arranged or by which the inlet portion is formed. It goes without saying that, in addition to the widening in the lateral direction, the channel-like portion can have an incline. The incline can, in particular, be provided in a direction that corresponds to the angle of the inlet portion to the inlet surface. Alternatively, the angle of inclination can be any angle different from the inlet angle. In this way, the distributor means can simultaneously constitute an oblique plane, in order to guide the liquid to be treated in an improved manner into the first chamber and over the gas exchanging means. The distributor means is therefore preferably inclined from the inlet portion toward the first chamber.

The distributor means can be formed integrally with the diaphragm seal and/or with the inlet portion and/or with the cover on the inlet side and/or with the inlet surface of the housing. As a result, fewer individual components need to be installed in the device according to the invention. This can allow for a simplified production and maintenance process. Moreover, the reliability of the device can be increased by the consequently reduced need for seals between individual components.

The developments described above can be realized in yet other embodiments on the outlet side also of the device with respect to the outlet portion. Such modifications of the outlet portion can result in an improved outflow of the liquid from the device according to the invention. This can, in particular, also make possible that—for example, when using the device as a gas exchanger in the form of an artificial lung—a pumping power provided externally for maintaining the circulation of the liquid can be reduced, or that an external pump can be dispensed with completely.

In a development of the invention, a third chamber can, moreover, be formed in the first chamber, in addition to the first chamber. The third chamber can in this case also be formed as a part of the gas exchanging means. The third chamber can be separated from the first chamber by at least one liquid-permeable membrane and serve to extract one or more components of the biological liquid. For the device according to the invention, this can open up additional areas of application, in which specific liquid components are also extracted from the biological liquid, or even added to the liquid.

In alternative embodiments, the third chamber can also be designed analogously to the second chamber, but in a spatial arrangement deviating from the second chamber. For example, the second and the third chambers can respectively have a plurality of layers of a fiber bundle, which layers respectively consist of a plurality of hollow fibers arranged in parallel. The individual layers of the second and third chambers can then be arranged to be alternately stacked, wherein the hollow fibers of a layer are not oriented in parallel to the hollow fibers of an adjacent layer. The hollow fibers of a layer can, in particular, be oriented at a right angle to the direction of extension of the hollow fibers of an adjacent layer. In this way, the contact surface of the biological liquid with the second and third chambers can be increased.

It goes without saying that the embodiments indicated above can also be implemented in combination with one another without moving away from the inventive concept, unless this is expressly excluded.

According to another aspect of the present invention, the device according to the invention can be designed as a gas exchanger that can be used in an artificial lung or in a bioreactor.

It is thus basically possible to provide a device for treating a biological liquid with various connectors and geometrically differently designed gas exchanging elements. The objective of a device for treating a biological liquid within the meaning of the present invention is to deplete a biological liquid—in particular, blood—of carbon dioxide or other gases, or other, even more complex molecules, and/or to enrich it with oxygen or other gases or other molecules. Naturally, a depletion of other components of the liquid can also basically be achieved.

Particularly in the treatment of complex liquids that, among other things, contain living cells such as blood, it is advantageous to reduce any external stress to a minimum. This also includes, for example, that an inflow of a gas exchanging device take place preferably such that a laminar, constant flow of the biological liquid is maintained. In doing so, turbulences are preferably avoided, and an even, homogeneous inflow of the gas exchanging portion is advantageously brought about. Particularly in a case in which the biological liquid is blood, an inflow can preferably take place with a physiological flow velocity of the liquid. In addition to the form described above, this can, naturally, also take place in other ways in accordance with preferred embodiments of the invention. It is thus already advantageous if the inflow of the gas exchanging means—in particular, of a fiber mat—allows for a continuous flow.

Within the meaning of the invention, the term "fiber mat" is also used here and below representatively for a gas exchanging means. This term, "fiber mat," denotes single-layer or multi-layer structures, which can, for example, be made of hollow fibers that are formed in a mat-like arrangement. Fiber layers, or individual fiber mats, layered one above the other, can respectively be arranged to be rotated by an angle relative to a layer located underneath, whereby a round fiber mat arrangement or a round fiber bundle can be created. Depending, in particular, upon the purpose and the intended size, fiber mats can generally be made of several individual fiber layers, i.e., individual fiber mats, or consist of only a single layer.

Such fiber mats, which, in particular, have a rectangular basic form and which can extend, in the form of a fiber mat layer arrangement, in a height direction over a certain height, are known from the prior art. Such fiber mat arrangements or fiber bundles have, in this case, a cuboidal shape. The problem with such cuboidal fiber mat arrangements can in this case, however, consist in that an at least largely even flow cannot be ensured when assuming a corresponding shape of the cavity in the gas exchanging device, i.e., a likewise cuboidal cavity. Particularly along the edges and in the corner portions of the cavity, turbulences of the liquid can increasingly occur, which can result in a degradation of the liquid. The efficiency of the gas exchange in these edge regions can thus be reduced.

It is, however, precisely an objective to obtain a gas exchange rate as high as possible, to avoid a degradation of the liquid, and/or to achieve as efficient a utilization as possible of the gas exchanging element.

In this respect, it is conceivable, for one thing, to arrange a gas exchanging means that is round in its basic form— preferably, a circular gas exchanging means—in such a rectangular cavity. In this way, edge effects in a cuboidal cavity can affect the gas exchange rate in the gas exchanging means less, or not at all.

In addition, it is possible to provide a round—preferably, circular—cavity in which a cuboidal or a round gas exchanging means—in particular, a fiber mat or a fiber mat arrangement—is arranged. The contour of the gas exchanging means corresponds in this case ideally to the shape of the cavity, so that as large a volume as possible of the cavity can be filled with the gas exchanging means. This can, ideally, enlarge the volume in the cavity available for the gas exchange.

The use of a cuboidal fiber mat or fiber mat arrangement in a round cavity can make it possible to avoid edge effects on the wall of the cavity, where the flow velocity of the liquid is necessarily at a minimum. An improvement in the efficiency of the gas exchanging element, i.e., in this case, the fiber mat or fiber mat arrangement, can thus be achieved.

The shape of the cavity—for example, for accommodating the fiber mat or fiber mat arrangement in the device—as well as the shape of the fiber mat or the fiber mat arrangement itself, can in this case be round, or even circular. A "round" shape of the fiber mat or the fiber mat arrangement or of the cavity can correspond to any shape that has a continuous contour, i.e., a contour without the formation of edges and corners. A round shape can, in particular, also include an elliptical design. In addition, a round shape can also include other symmetrical or asymmetrical shapes, e.g., shapes that allow for an improved flow around the fiber mat or the fiber mat arrangement, i.e., generally around the gas exchanging means. In addition, the term, "round shape," can also be understood, for example, to mean a cavity that has rounded corners and edges. The shape of the gas exchanging means can in this case also vary—for example, in a height direction along a cross-section of the gas exchanging means.

Incidentally, mixed shapes are also conceivable for the shape of the gas exchanging means, with one or more corners and otherwise round or rounded portions. Basically, the shapes of the gas exchanging means are thus not limited, and the totality of shapes can be arranged in a cavity of a gas exchanging device as long as the necessary connectors are provided, and the specific dimensions of the cavity and of the gas exchanging means allow for an insertion of the gas exchanging means into the cavity. The shapes of the cavity of the first chamber and of the gas exchanging means can, in this case, also deviate from one another.

It also goes without saying that, following the inventive concept, a connector for the supply line of the biological fluid into the gas exchanging portion can also be arranged orthogonally to the surface. This can, for example, be the case when the gas exchanging means is arranged at an incline—in particular, an incline at an acute angle—relative to the surface of the gas exchanging device. The specific shape of the gas exchanging means itself can also already bring about an inclined inflow of the liquid relative to the gas exchanging means, e.g., if an oblique plane results on the surface of the gas exchanging means in case of an inhomogeneous height dimension of the gas exchanging means. Incidentally, it is also conceivable that the cavity for accommodating the gas exchanging means be arranged in an inclined position relative to the surface of the gas exchanging device on which the connector for the inflow of liquid is formed.

The housing preferably has a prismatic shape, in which the lateral surfaces of the housing are designed as prismatic surfaces, wherein the shape of the housing is compact—in particular, flat—and wherein a blood inlet is arranged on an end face of the prismatic housing designed as an inlet surface.

Alternatively, the device for treating a biological liquid advantageously comprises an—in particular—prismatic housing with a first chamber, which forms a cavity and which is designed to receive the liquid to be treated, and at least one gas exchanging means, which is arranged at least partly in the first chamber, wherein an inlet portion for the inlet of the liquid to be treated into the first chamber is formed in a surface of the housing—in particular, a cover of the housing. The inlet portion in this case extends at an acute inflow angle relative to the surface of the fiber bundle.

It is advantageous if the inflow angle is less than 45°—preferably, less than 25°—particularly preferably, has a value of 5° to 20°, and is, especially, 15°.

It is furthermore advantageous if flow guiding surfaces are arranged on both sides of the channel-like portion, which flow guiding surfaces have a slope opposite to the slope of the channel-like portion so that a first axis defined by the channel-like portion and a second axis defined by the flow guiding surfaces intersect at an acute angle of preferably 5° to 20°. By means of the two flow guiding surfaces, a turbulence-free distribution of the incoming fluid flow is achieved. In the case where the supplied liquid is blood, blood coagulation (agglutination) and blood damage (hemolysis) are effectively prevented thereby. A very good, permanent gas exchange effectiveness with respect to the gas exchanging surface is achieved.

Basically, it is, naturally, also conceivable that an orthogonal inflow be also brought about when using a round gas exchanging means. This alone already brings about the advantage that edge effects, which can bring about a reduction in the efficiency of the gas exchange or a degradation of the liquid—in particular, in a round cavity—can be reduced. The inflow can in this case basically also take place orthogonally relative to the inlet surface of the housing and/or relative to the gas exchanging means itself—in particular, to a fiber mat or a fiber mat arrangement. An orientation of the gas exchanging means in the cavity can in this case also be an inclined orientation—for example, with respect to the inlet surface.

The production of such round or rounded fiber mats and fiber mat arrangements, or such fiber mats and fiber mat arrangements with an inhomogeneous cross-section, can in this case take place in a way similar to what is known for the production of cuboidal fiber mats.

BRIEF DESCRIPTION OF THE DRAWINGS

The invention and advantageous developments thereof are now explained with reference to certain exemplary embodiments illustrated in the attached drawings, in which equivalent features are given the same reference symbols. The following is shown.

DETAILED DESCRIPTION OF THE INVENTION

Figure 1:
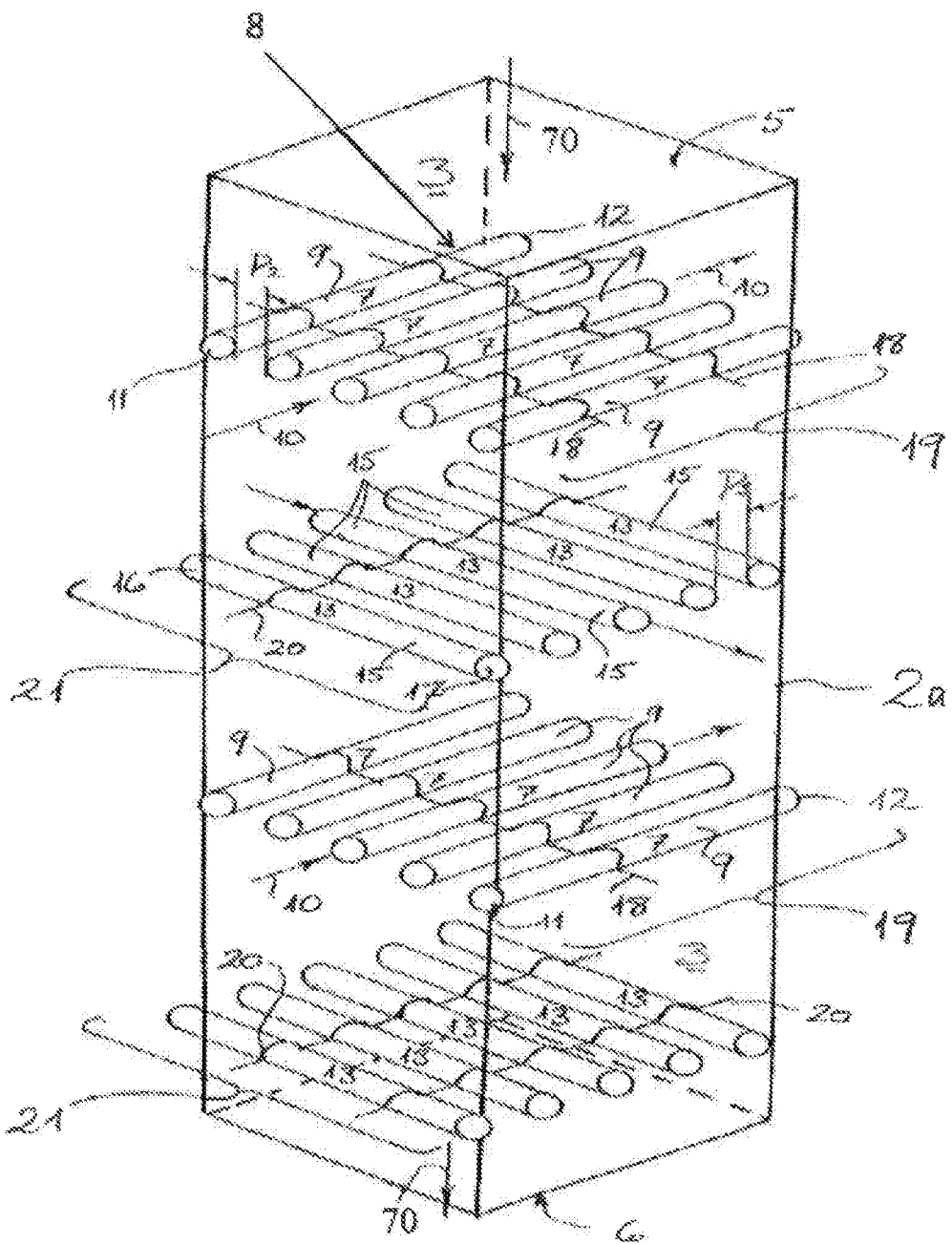
FIG. 1 a schematic illustration of a section of a fiber bundle for a device according to an embodiment of the invention, FIG. 2 a schematic illustration of a device according to the invention according to an embodiment of the invention, FIG. 3 an enlarged cross-sectional view of a connector for a device according to an embodiment of the invention, FIG. 4 a schematic illustration of a cover for a device according to an embodiment of the invention, FIG. 5 a schematic illustration of another cover for a device according to the invention, according to another embodiment of the invention, FIG. 6 a cross-sectional view of the cover from FIG. 5 in a section along the line VI-VI in FIG. 5, FIG. 7 a perspectival cross-sectional view of the cover from FIG. 5 in a section along the line VII-VII in FIG. 5.

For better understanding of the present invention, FIG. 1 shows an example of the structure of a gas exchanging means—here, in the form of a multi-layer fiber bundle made of two layer types in the form of differently oriented fiber mats 19 and 21. In this case, FIG. 1 shows, for a basic understanding of the present invention, only a schematic view of the fiber bundle 18, with the fiber mats 19, 21 in a type of exploded view of the layers. Due to the schematic character of a subregion of the fiber bundle 18, FIG. 1 does not allow for any conclusions as to the actual shape of a fiber bundle—as to how it is to be used in a device according to the invention—in particular, not with respect to the shape, proportions, or design of the fiber bundle layers or their specific characteristics. In an integrated structure of the fiber bundle, an arrangement of fiber mats, which is also descriptively called a fiber bundle here, is [sic] from the individual fiber layers—also called fiber mats. The fiber bundle 18 has a surface 8 defined by a first fiber mat 19, 21. A device 1 according to the invention, as it is, moreover, also illustrated in FIG. 2, has a housing 2 that surrounds or partly defines a first chamber 3. The first chamber 3 is provided for receiving a biological liquid, such as blood, and is designed in the illustrated embodiment as a flow-through chamber. The biological liquid or the blood flows in the direction indicated by the arrows 70 through an inlet surface 5 in the housing 2 into the first chamber 3, and leaves the first chamber 3 through an opposite outlet surface 6. The housing 2 preferably consists of a plastic, such as polyethylene or polyurethane, that does not chemically react with the biological liquid. The housing 2 has a prismatic shape, in which the lateral surfaces are designed as prismatic surfaces 4, the base surface as outlet surface 6, and the end surface as inlet surface 5. The shape of the housing 2 is in this case flat or compact, i.e., the height of the housing 2 between the outlet surface 6 and the inlet surface 5 is less than its lateral extent transversal to its height. The surface 8 of the fiber bundle 18 extends substantially in parallel to a plane defined by the inlet surface 5.

The device 1 furthermore has a tubular second chamber 7 which extends through the first chamber 3 and is substantially surrounded by the first chamber 3. The second chamber 7 is not visible in FIG. 2. A tubular wall delimits or surrounds the cavity of the second chamber 7. This wall is relatively thin and preferably consists of a plastic, and serves as support material for an outer layer, which, together with the wall, forms a gas-permeable and liquid-impermeable membrane 9. The second chamber 7 is provided to contain and conduct a fluid. In preferred embodiments, the fluid is a gas, such as ambient air, compressed air, a gas mixture enriched with oxygen, or highly concentrated or pure oxygen. The tubular wall in this case allows for a transfer of gas molecules between the first chamber 3 and the second chamber 7. In other words, the membrane 9 forms a separation surface or contact surface, on which an intimate contact between the molecular components of the blood and of the medium contained in the second chamber can occur or take place.

As in the case shown in FIG. 1, the second chamber 7 can be designed as a flow-through chamber. The gas-permeable and liquid-impermeable membrane 9 is, preferably, selectively permeable by carbon dioxide and/or oxygen. In special embodiments, the described invention is used to bring about an oxygenation, i.e., an enrichment with oxygen, of the biological liquid. It is, however, also alternatively conceivable that, depending upon the specific application, only a carbon dioxide reduction, i.e., a decarboxylation, takes place. Depending upon the desired application, a suitable gas is consequently selected, such as air enriched with oxygen or carbon dioxide-poor air, in order to bring about a gas exchange with the biological liquid.

The selected gas flows in the direction shown by arrow 10 in FIG. 1 through an inlet 11 into the second chamber 7, and leaves the second chamber 7 through an opposite outlet 12. The gas flowing through the second chamber 7 can in this case partly pass through the gas-permeable and liquid-impermeable membrane 9 into the liquid flowing through the first chamber 3. In addition, a gas portion dissolved in the liquid in chamber 3 can pass through the membrane 9 into the second chamber 7. In the case where the biological liquid is blood, an enrichment of the blood with oxygen or a depletion of the blood of carbon dioxide can thereby take place. In this way, a so-called ventilation or lung assistance process takes place at the membrane 9.

A pressure $P_1$ and/or the flow of the biological liquid or of the blood in the first chamber 3 can be selected or adjusted in relation to the pressure $P_2$ and/or the flow of the oxygen flowing through the second chamber 7. In this way, a desired transfer of oxygen into the liquid and/or of carbon dioxide out of the liquid can be achieved. It basically applies in this case that a gas exchange takes place from the side of the two chambers 3, 7 to the respective other chamber 7, 3 in which a higher partial pressure of the respective gas prevails. For this purpose, the blood can be conveyed through the first chamber 3 by means of a pump (not shown), for example, or it can also just flow through the first chamber 3 under the pressure of the circulatory system of the patient. Alternatively or additionally, precautions can also be taken, which affect a pressure-independent enrichment of a selected component in one of the chambers 3, 7, e.g., the reversible or irreversible bonding of gas molecules on correspondingly-used surfaces or components of respective fluids, i.e., of the biological liquid, or of the gas or the gases.

In special embodiments, the device 1 can further have a tubular third chamber 13 which extends, like the second chamber, through the first chamber 3 and is substantially surrounded by the first chamber 3. A tubular wall 14, which surrounds the cavity of the third chamber 13, is relatively thin and preferably consists of a plastic. As with the second chamber 7, the wall 14 serves as support material for an outer layer. In this case, it is conceivable that the third chamber is a chamber independent of the second chamber 7 and has a gas-permeable, liquid-impermeable membrane 15, which is permeable by the same or by different or additional gases as the membrane 9 between the first chamber 3 and the second chamber 7. In this way, a second independent gas supply can, for example, be coupled with the device, or, if needed, additional gases can be supplied to the device, or a depletion rate of gases from the biological liquid can be increased.

In special embodiments, the third chamber 13, together with the wall 14, can also form a liquid-permeable membrane 15, so that the tubular wall 14 allows for a transfer of liquid components between the first chamber 3 and the third chamber 13. In particular, this membrane 15 forms a separation or contact surface, which serves to extract one or more liquid components of the biological liquid. Other embodiments are, naturally, also conceivable, in which the wall between the first chamber 3 and the second chamber 7 forms a liquid-permeable wall 9.

The liquid-permeable membrane 15, which is located between the first and third chambers, can then act as a filter, via which smaller molecules, such as water, are pressed out of a biological liquid, such as blood, and larger molecules, such as protein and blood cells, are retained.

It is understood that the gas exchanging means of the device according to the invention can have one or more second chambers. It is further understood that the structure shown in FIG. 1 of a gas exchanging means in the form of one or more fiber bundles can indeed be advantageous for the invention or for developments of the invention. However, gas exchanging means with a different layer structure or without a layer structure are also conceivable within the scope of the invention—for example, in the form of porous structures. In this respect, the illustration of FIG. 1 shows only an exemplary gas exchanging means in the form of a fiber bundle for certain embodiments of the present invention.

In one embodiment of the present invention, as it is shown in FIG. 1, the second chamber 7 or the third chamber 13 has a plurality of tubular hollow fibers, as explained below. The housing 2 surrounds or defines, in this case, at least partly, the first chamber 3. The first chamber 3 is provided for receiving a biological liquid, such as blood, and is designed as a flow-through chamber. The first chamber 3 can also be an accommodation, inserted into the housing and corresponding to the opening in the housing, for accommodating the second and/or third chamber.

Figure 2:
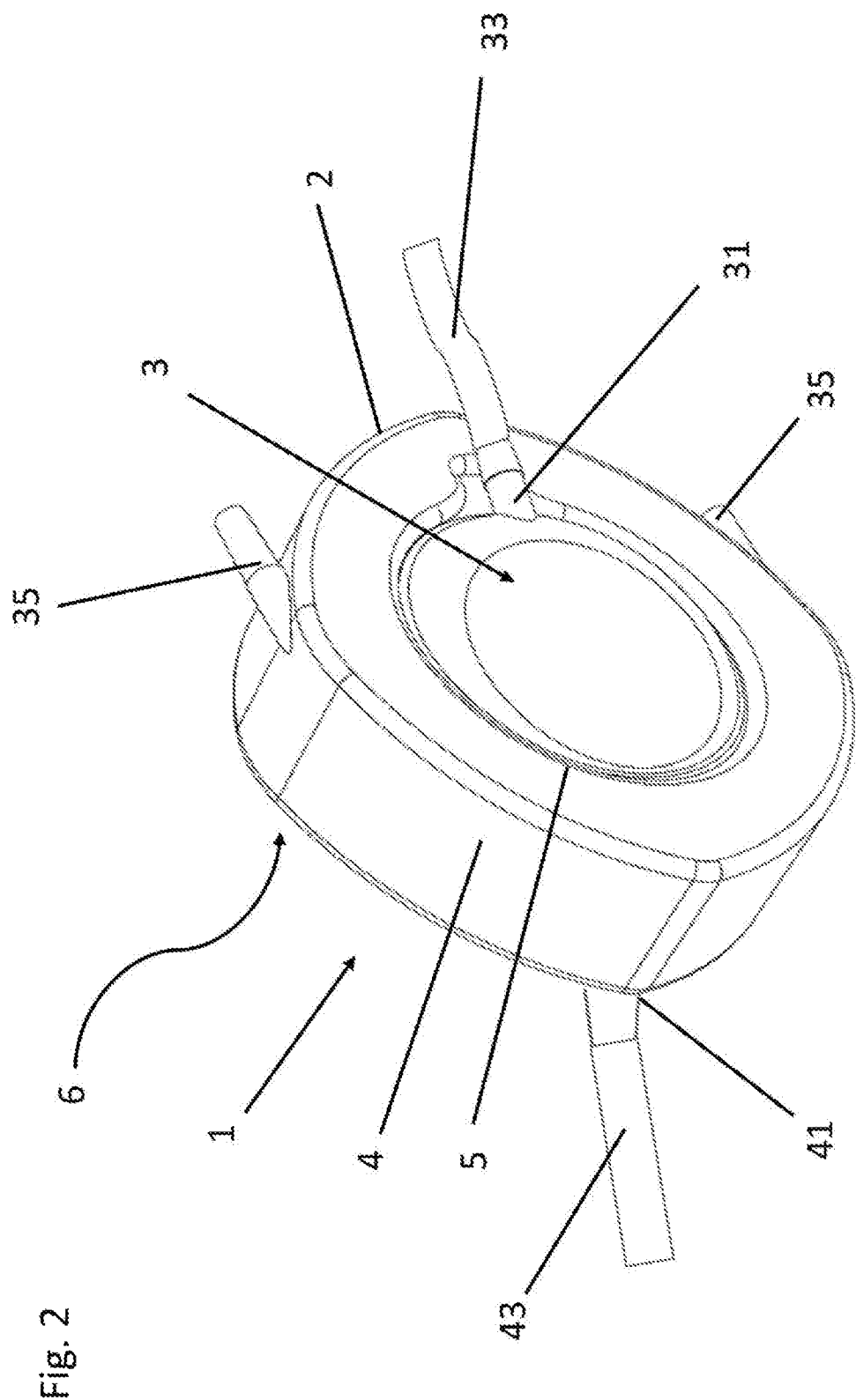

It must be noted that the first chamber 3 and the second chamber 7 or additional chambers 13 are provided as an integrated, sterilely-closed system. In this case, a housing 2a of the first chamber would be inserted into a corresponding opening of the housing 2 of the gas exchanging device. This case is shown in FIG. 2. Alternatively, a fiber bundle can also be inserted into the housing 2 of the gas exchanging device 1, wherein the inner wall of an opening of the gas exchanging device 1, or the inner wall of an insert into this opening, defines the first chamber 3.

As shown in FIG. 1, the device 1 has a plurality of tubular second chambers 7 arranged next to each other in rows. The second chambers 7, i.e., the gas exchanging means, extend in parallel through the first chamber 3 and are substantially surrounded by the first chamber 3. The tubular walls surrounding the cavities of the second chamber 7 can be designed in the form of hollow fibers made of polymethylpentene (PMP—also known under the brand name TPX®)—for example, foam TPX. In other embodiments, other materials can be used in the same way. The walls of the second chamber 7 and its outer surfaces or layers form gas-permeable and liquid-impermeable membranes 9, so that a transfer of gas molecules between the first chamber 3 and the second chambers 7 located inside the hollow fibers is made possible.

The second chambers 7 are provided for receiving a gas, such as oxygen or ambient air, and are also designed as flow-through chambers. The gas-permeable and liquid-impermeable membranes 9 can in this case be designed to be selectively permeable by oxygen and/or carbon dioxide. In the device shown in FIG. 1, the selected gas flows in the direction shown by arrow 10 through inlets 11 into the second chambers 7, and leaves the second chambers 7 through opposite outlets 12. As before, a portion of the oxygen that flows through the second chambers 7 can pass through the gas-permeable and liquid-impermeable membranes 9 into the liquid flowing through the first chamber 3. This can result in an enrichment of the liquid with oxygen. In a similar way, a transfer or removal of carbon dioxide from the liquid—in particular, blood—through the membranes 9 into the second chambers 7 can take place, so that a so-called ventilation or lung assistance process occurs.

The hollow fibers arranged next to each other in a row/plane and forming the second chambers 7, e.g., TPX fibers, are connected to each other with warp threads 18 in a textile engineering process. This results in a kind of fiber mat 19 with defined distances $D_2$ between the fibers. This distance $D_2$ between the fibers serves to allow the blood flowing through the first chamber 3 to flow through the mat 19 and to thus achieve a maximum contact with the contact surfaces of the membrane 9. In this exemplary embodiment, the individual hollow fibers have an outer diameter in the range of 100 μm to 1 mm—preferably, in the range of 200 μm to 600 μm (for example, approximately 400 μm)—and are arranged in each row or plane next to each other with a distance $D_2$ in the range of 100 μm to 500 μm. This distance can be selected arbitrarily. It is therefore clear that a plurality of fibers can be placed next to each other and processed into mats 19. The dimensions of the fiber membrane mat 19 are, for example, approximately 10 cm×15 cm.

In some embodiments of the invention, the fiber mats, hereinafter also called fiber membrane plates, have a round shape, in order to correspond to a cylindrical cavity in the housing. These fiber membrane plates are, in particular, arrangements of several fiber mats layered one above the other. Naturally, it is also conceivable that cuboidal or cubical fiber membrane plates with a cylindrical cavity are used, or that round or substantially cylindrical fiber membrane plates with a cubical or cuboidal cavity of the device according to the invention are used.

If the hollow fibers are processed into mats or fiber mats 19, 21, these mats 19 can subsequently be processed further by stacking them one above the other. In FIG. 1, only two layers or mats 19 of the second chambers 7 extending in parallel are shown, and they are stacked one above the other. The person skilled in the art, however, understands that a plurality of such mats 19 can be provided, one above the other, in the first chamber 3. Even though it is not shown in FIG. 1, the ends of the fibers forming the second chambers 7 are bundled together or interconnected. In this way, the individual inlets can be supplied with gas, e.g., ambient air or oxygen, via a common inlet 11. Analogously, the individual outlets transition into a common outlet 12. This preferably applies not only to the second chambers 7 of the individual mats 19, but to all second chambers 7 in all mats 19. This so-called "interconnection" of the fibers with the same orientation preferably takes place in a casting process—for example, using polyurethane. In this case, the ends of the fibers in the outer region of the fiber stack are cast in liquid plastic. After hardening of the plastic, the fibers are then cut slice-by-slice from the outside, until the interior of the fibers is opened. A common fluid supply into the individual fibers or chambers is thus achieved.

In addition, the device 1 in FIG. 1 has several tubular third chambers 13 which extend, like the second chambers 7, in parallel through the first chamber 3 and are substantially surrounded by the first chamber 3. While the hollow fibers in some embodiments can be designed in the same way as the hollow fibers of the mats 19 described above, it is also possible in special embodiments that the tubular walls 14, which surround the cavities of the third chambers 13, be designed in the form of hollow fibers made of polyether sulfone (PES). In this case, the walls 14 of the hollow fibers with their outer surfaces form liquid-permeable membranes 15, which can allow a transfer of liquid components between the first chamber 3 and the third chambers 13 located inside the hollow fibers. In particular, the membranes 15 can form separation or contact surfaces, which serve to extract one or more liquid components of the biological liquid.

As with the hollow fibers of the first mats 19, the hollow fibers arranged next to each other in a row or plane and forming the third chambers 13—in this case, PES fibers or TPX fibers—are connected to one another with warp threads 20 in a textile engineering process. This, again, results in a kind of fiber mat 21 with defined distances $D_3$ between the fibers. This distance $D_3$ between the fibers also serves to allow the liquid—in particular, blood—flowing through the first chamber 3 to flow through the mat 21, and to thus achieve a maximum contact with the surface of the membranes 15. FIG. 1 shows only two layers or mats 21 of third chambers 13, and illustrates them as layers 21 stacked one above the other. In this exemplary embodiment, as with the second chambers 7, the individual fibers have an outer diameter in the range of 100 μm to 1 mm—preferably, in the range of 200 μm to 600 μm—and are arranged in each row or plane next to each other with a distance $D_3$ preferably in the range of 100 μm to 500 μm. A plurality of fibers can therefore be placed next to each other and processed into mats 21. The dimensions of each fiber membrane mat 21 are also approximately 10 cm×15 cm, wherein various—in particular, round—shapes are also possible for such multilayer fiber membrane mats 21, analogously to the explanations above.

The processing of the individual fiber membrane mats 21 otherwise takes place as for the fiber membrane mats 19 as described in detail above. Such fibers or fiber mats are, for example, basically known from WO 2010/091867.

The longitudinal alignment of the preferably in-parallel arranged second chambers 7 extends orthogonally to the longitudinal alignment of the in-parallel arranged third chambers 13, and the layers or mats 19, 21 of the TPX or PES fibers are, in this example, layered alternately, directly one on top of or above the other. This results in a compact fiber mat. The mats or fiber mats 19, 21 are, preferably, directly placed one on top of the other, so that they are in contact with each other. FIG. 1 shows the layers or mats 19, 21 spaced far apart in an exploded view, in order to allow for a clearer explanation of the invention.

The explanations above show that the device according to the invention can be used for a plurality of applications. A detailed description of the invention with reference to a preferred embodiment is given below.

According to FIG. 2, the device 1 is designed as an artificial lung, which is illustrated schematically in FIG. 2. The housing 2 of the device 1 is in this case designed to be substantially cuboidal, with roundishly extending lateral edges. In a corner region of the inlet surface 5, an inlet portion 31 in the form of a connector is formed on the inlet surface 5 of the housing 2. On one side, facing away from the housing 2, of the inlet portion 31, a supply line 33 is formed. In a similar way, an outlet portion 41 with a discharge line 43 is provided on the outlet surface 6 of the housing 2. As a result of the perspective illustration of FIG. 2, the outlet surface 6 can, however, not be seen in the figure.

Furthermore, another connector 35 is also provided on or adjacent to the inlet surface 5. The connector 35, in particular, branches off from a prismatic surface 4 of the housing 2. The connector 35 can have various functions. For example, the connector 35 can serve to supply gas to the gas exchanging means, i.e., essentially to the second chamber 7 or the third chamber 13, in a manner corresponding to the embodiment of the gas exchanging means shown in FIG. 1. Moreover, a fluid removal can take place by means of the connector 35—in particular, in a fluid circulatory system with several connectors 35—as illustrated in FIG. 2.

Figure 3:
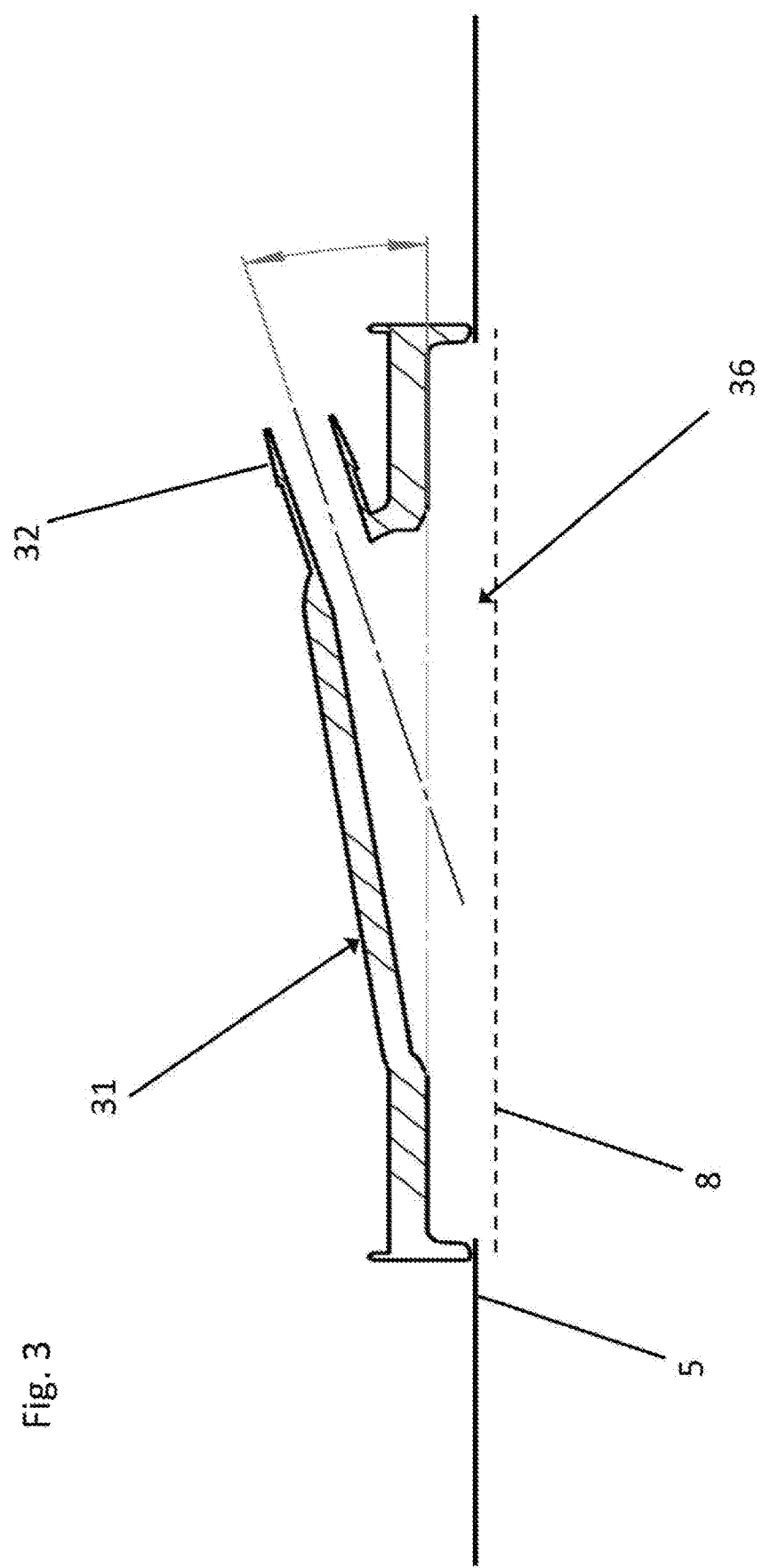

FIG. 3 shows an inlet portion 31 for a device 1 according to the invention. The inlet portion 31 is formed on the inlet surface 5 of the housing 2. On one side, facing away from the inlet surface 5, of the inlet portion 31, a connector portion 32 is provided. The connector portion 32 serves to connect the inlet portion 31 to a fluid supply, i.e., for example, a tube as supply line 33. In the embodiment shown here, the inlet portion serves, in particular, to supply a biological liquid, such as blood. In the inlet surface 5 is provided an opening 36, which forms the inlet of the liquid into the first chamber 3 (not shown in FIG. 3).

As can be seen in FIG. 3, the inlet portion is designed and arranged at an acute angle relative to the inlet surface 5. In the illustrated embodiment according to FIG. 3, this inlet angle is approximately 15°. The inlet angle can, however, vary, wherein the inlet angle is preferably less than 45°, more preferably, less than 25°, and, in particular, between 15°-20°. As a result of the parallelism of the surface 8 of the fiber bundle 18 arranged in the housing 2 to the inlet surface 5 or to the plane defined by it, the inlet portion 31 extends at an acute inflow angle α relative to the surface 8 of the fiber bundle 18. This inflow angle α is preferably less than 45°, more preferably, less than 25°, and, in particular, has a value of 5° to 20°. In the present exemplary embodiment, the inflow angle α has a value of 15°.

In this way, a tangential inflow of the biological liquid is made possible. Moreover, a tangential conduct of the supply and discharge lines can be made possible in this way. This can in turn allow for an installation in a compact format—for example, in a portable device.

Figure 4:
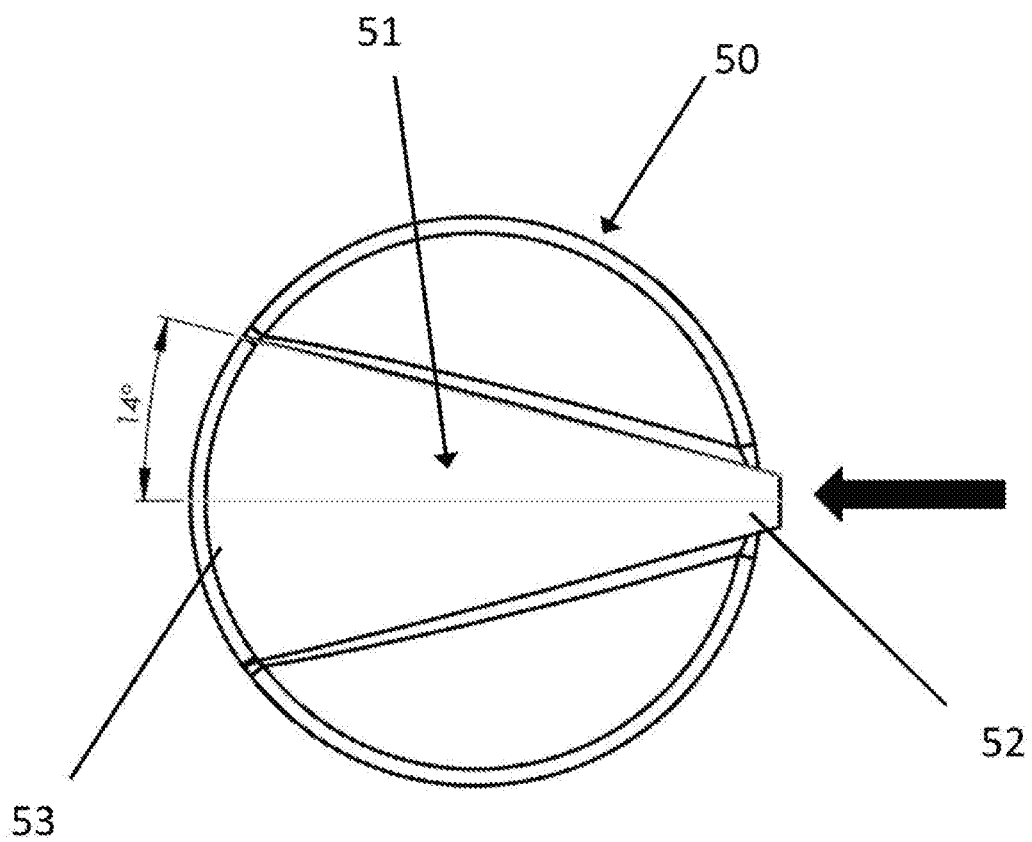

FIG. 4 shows a cover 50 of the device according to the invention. The cover 50 is in this case, in particular, designed such that it can be arranged below the opening 36 shown in FIG. 3, so that the liquid supplied through the inlet portion 31 is guided onto the cover 50. The cover 50 in this case has a channel-like portion 51. "Channel-like" in this case is to be understood such that the channel-like portion 51 constitutes a recess in the cover 50, which predetermines a flow direction of the liquid guided onto the cover 50. The arrow in FIG. 4 denotes in this case a flow direction of the supplied liquid along the cover 50.

As can also be seen in FIG. 4, the channel-like portion 51 has a first end 52 and a second end 53. The channel-like portion 51 is designed such that it expands in the flow direction from its first end 52 to its second end 53. This results in a distribution of the supplied liquid over a larger area and thus allows for a more homogeneous flow into the components downstream of the cover 50, i.e., essentially, the first chamber 3 with the gas exchanging means.

The cover 50 or the channel-like portion 51 of the cover 50 is in this case preferably designed such that the channel-like portion 51 expands at an angle of between 10°-20°. In the embodiment shown in FIG. 4, the expansion angle, i.e., the angle by which the channel-like portion 51 expands in accordance with this definition, is 14°. The angle which the individual legs of the channel-like portion 51 enclose is double the expansion angle, i.e., 28°, in the embodiment shown.

While the inlet portion 31 and the cover 50 are designed as individual components in the embodiments shown in FIGS. 3 and 4, it is conceivable that the inlet portion 31 also be designed to be integral with the cover 50. In this case, the cover 50 could, for example, be arranged in the opening 36 of the inlet surface 5 such that the liquid supplied through the inlet portion 31 is directly fed into the chamber 3. In this case, the cover can also have an oblique plane that, following the incline of the inlet portion, for example, leads from the inlet surface 5 through the opening 36 into the first chamber.

Moreover, in the embodiment according to FIG. 4, the cover is also, as a result of the expanding channel, at the same time a diaphragm seal component, since the inflowing liquid is distributed over a larger area, and the flow pressure is thus reduced. At the same time, again, the cover according to the embodiment according to FIG. 4 also constitutes a distributor means for the inflowing liquid.

In alternative embodiments, the cover 50 can also be designed to be separate from a diaphragm seal or from a distributor means—for example, only as a covering of the inlet surface 5 on the outside of the inlet surface 5 or on the inside of the inlet surface 5. In this case, a separate diaphragm seal and/or a separate distributor means could be provided in the device.

Figure 5:
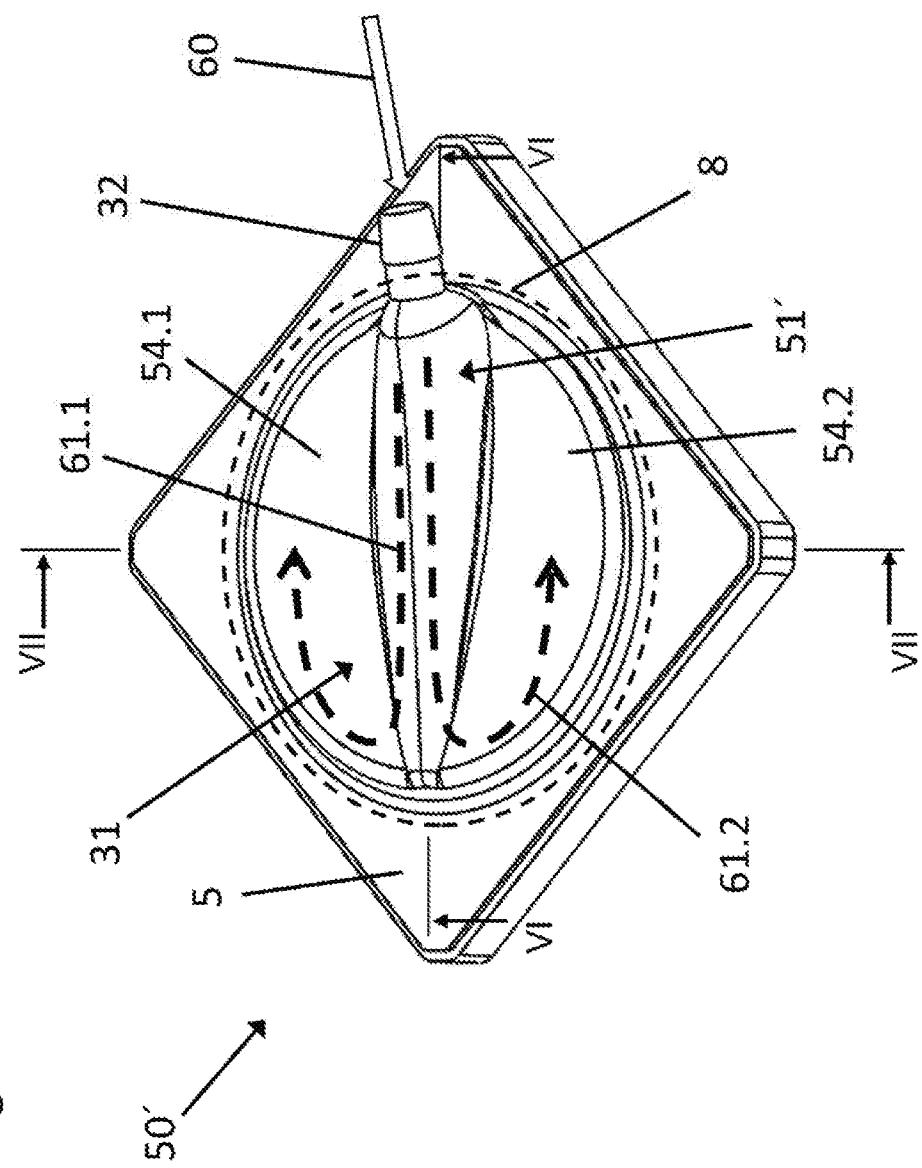
Figure 6:
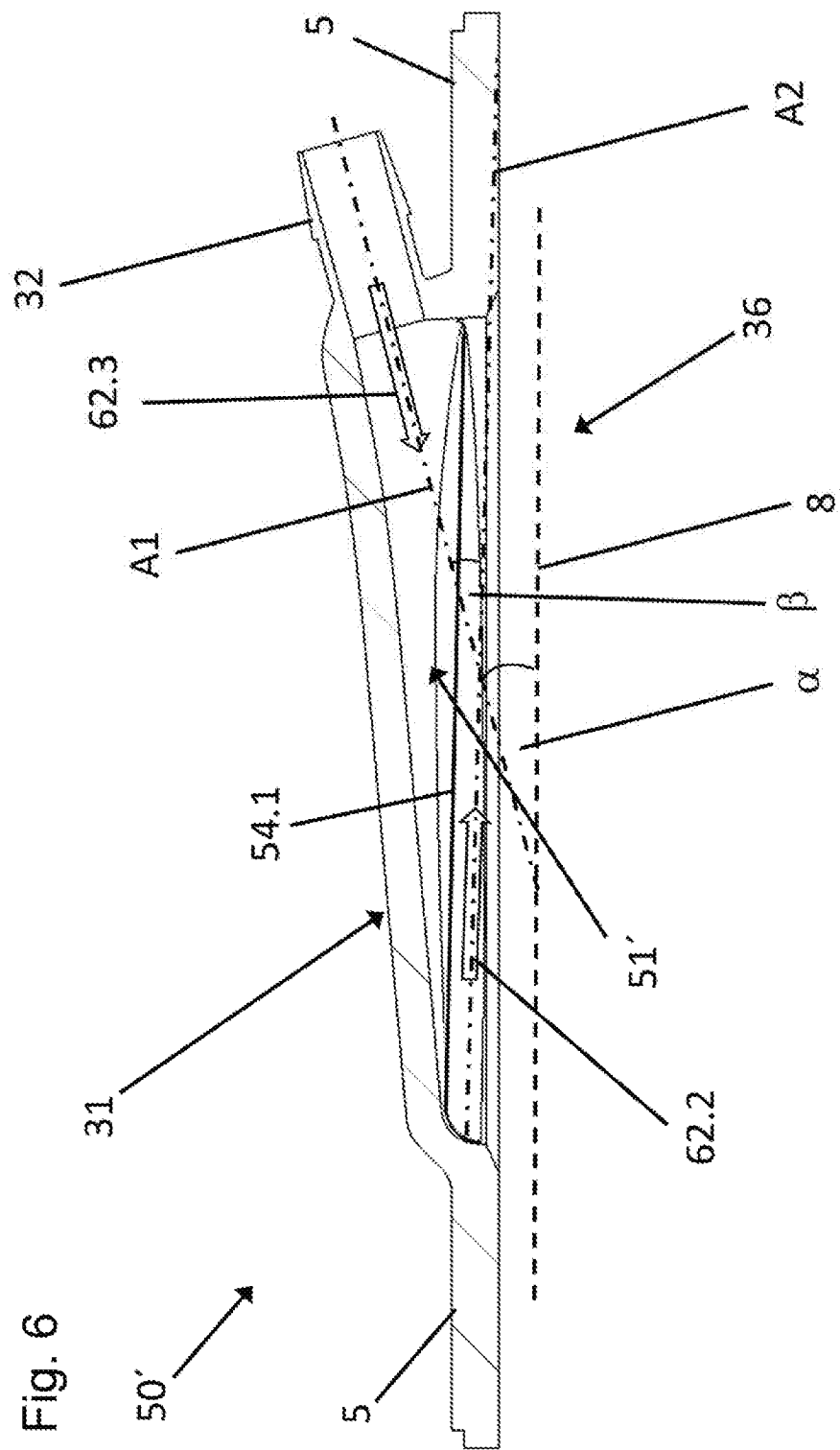

An alternative cover 50' of the device according to the invention is illustrated in FIGS. 5 through 7. The cover 50' is either designed such that it can be arranged below the opening 36 shown in FIG. 3, so that the liquid supplied through the inlet portion 31 is guided onto the cover 50', or it is designed such that it forms the entire surface/inlet surface 5 of the prismatic housing 2. The cover 50' in this case again has a channel-like portion 51'. "Channel-like" in this case is to be understood such that the channel-like portion 51' constitutes a bulge in the cover 50', which predetermines a flow direction of the liquid guided into the cover 50'. The arrow 60 in FIG. 5 in this case denotes an inflow direction of a liquid guided into the cover 50', and the arrows 61.1 and 61.2 (in FIG. 5) and the arrows 62.1 through 62.3 (FIGS. 6 and 7) denote the further course of the flow of the inflowing liquid between the cover 50' and the fiber bundle located below it inside the housing, which fiber bundle is indicated in FIGS. 5 through 7 by the position of the surface 8.

In this embodiment, the channel-like portion 51' of the inlet portion 31' is arranged at an acute inlet angle relative to the inlet surface 5, as can be seen, in particular, in FIG. 6. In the illustrated embodiment according to FIG. 6, the inlet angle is approximately 15°. The inlet angle can, however, vary, wherein the inlet angle is preferably less than 45°, more preferably, less than 25°, and, in particular, between 15°-20°.

As a result of the parallelism of the surface 8 of the fiber bundle 18 arranged in the housing 2 to the inlet surface 5 or to the plane defined by it, the channel-like portion 50' of the inlet portion 31' extends at an acute inflow angle α relative to the surface 8 of the fiber bundle 18. This inflow angle α is preferably less than 45°, more preferably, less than 25°, and, in particular, has a value of 5° to 20°. In the present exemplary embodiment, the inflow angle α has a value of 15°.

On both sides of the channel-like portion 50' are respectively located flow guiding surfaces 54.1 and 54.2, which have a slope (arrow 62.2 in FIG. 6) opposite to the slope (arrow 62.3 in FIG. 6) of the channel-like portion 50', so that a first axis A1 defined by the channel-like portion 50' and a second axis A2 defined by the flow guiding surfaces 54.1 and 54.2 intersect at an acute angle β of approximately 5° to 20°. In the present exemplary embodiment, the acute angle β has a value of 16.35°. The slope of the two flow guiding surfaces 54.1 and 54.2 (arrow 62.2 in FIG. 6) is preferably 1° to 5°. In the present exemplary embodiment, the slope (which corresponds to the angle of the flow guiding surfaces 54.1 and 54.2 to the surface 8 of the fiber bundle 18) is 1.35°. By means of the two flow guiding surfaces 54.1 and 54.2, a turbulence-free distribution of the incoming fluid flow is achieved. In the case where the supplied liquid is blood, blood coagulation (agglutination) and blood damage (hemolysis) are effectively prevented. A very good, permanent gas exchange effectiveness with respect to the gas exchanging surface is achieved.

As the person skilled in the art incidentally understands, additional connectors can be provided on the surface of the device in the same or in a similar manner. The structure of the device according to the invention thus allows for a plurality of possible simultaneous treatments of a liquid—in particular, of a biological liquid.

According to a special embodiment of the present invention, only a decarboxylation without simultaneous oxygenation is to be performed by the device according to the invention. Since a basic objective is to keep extracorporeal volume flows as low as possible, e.g., during the removal and return of blood into a body, the volume flows for such $CO_2$ removal systems are generally in the range below 2 $dm^3/min$ (2 L/min)—preferably, at approximately 0.3-1 $dm^3/min$ (approx. 0.3-1 L/min). In order to ensure a sufficient flow and an effective gas exchange at such low volume flows, the dimensioning of the fiber bundle or the cavity is crucial. When optimizing the dimensioning, a compromise must be found between competing requirements, such as a larger gas exchanging surface for an effective gas exchange, a compact construction for better mobility and portability, a homogeneous flow distribution and thus a low pressure loss and low shearing forces, as well as of hemocompatibility in order to increase the period of use of the device.

According to an embodiment of the invention, a diameter of 70 mm and a stack thickness of the gas exchanging means—in this case, the fiber bundle—of 25 mm were selected for the cavity of the gas exchanger, i.e., the first chamber, based upon these considerations and corresponding calculations. This results in a gas exchanging surface of approximately 0.6 $m^2$ in this particular embodiment. These dimensions represent a possible acceptable ratio with respect to the shearing forces and pressure losses occurring in the gas exchanger. These dimensions furthermore result in a sufficient $CO_2$ reduction in the case of low volume flows.

It goes without saying, however, that the present invention is not limited only to a decarboxylation. Alternative embodiments are, naturally, also conceivable in this case, without moving away from the basic idea of the invention claimed in the claims.

LIST OF REFERENCE SYMBOLS

1 Gas exchanging device
2 Housing
3 First chamber
4 Prismatic surfaces (of the housing)
5 Inlet surface/surface of the housing
6 Outlet surface
7 Second chamber
8 Surface of the fiber bundle
9 Membrane
10 Arrow
11 Inlet
12 Outlet
13 Third chamber
14 Wall 15 Membrane
18 Fiber bundle
19 Fiber mat
21 Fiber mat
31 Inlet portion
32 Connector portion
33 Supply line
35 Connector
36 Opening
41 Outlet portion
43 Discharge line
50 Cover
50' Cover
51 Channel-like portion
51' Channel-like portion
52 First end
53 Second end
54.1 Flow guiding surface
54.2 Flow guiding surface
60 Arrow
61.1 Arrow
61.2 Arrow
62.1 Arrow (flow direction)
62.2 Arrow (flow direction/slope)
62.3 Arrow (flow direction/slope)
A1 First axis
A2 Second axis
α Inflow angle
β Acute angle

The invention claimed is:

1. A device for treating a biological liquid, comprising:
a housing with a first chamber defining a cavity and which is adapted to receive a liquid to be treated, the housing having a first surface;
at least one gas exchanger at least partly disposed in the first chamber, the at least one gas exchanger comprising a fiber bundle formed by a plurality of hollow fibers at least partly disposed in the first chamber;
an inlet portion defined in the first surface of the housing, the inlet portion defining an inlet to the first chamber for the liquid to be treated, the inlet portion being formed at an acute angle relative to the first surface of the housing, the inlet portion formed on the first surface of the housing such that a biological liquid guided through the inlet portion is guided into the first chamber of the gas exchanger, the inlet portion extending and guiding the biological liquid at an acute inflow angle onto a surface of the fiber bundle, and the surface of the fiber bundle being essentially parallel to the first surface of the housing.

2. The device according to claim 1, wherein the at least one gas exchanger has at least one second chamber, the first chamber and the second chamber being spatially separated by at least one semi-permeable membrane, the at least one semi-permeable membrane adapted to transfer at least one predetermined molecule type between the first chamber and the second chamber through the at least one semi-permeable membrane in order to treat the biological liquid.

3. The device according to claim 1, wherein the housing further comprises a second surface defining an outlet portion for the outlet of the biological liquid from the device, the outlet portion being arranged at an acute angle relative to the second surface of the housing.

4. The device according to claim 3, wherein the angle of the inlet portion and/or of the outlet portion relative to the respective surface of the housing is in the range of 15°-20°.

5. The device according to claim 1, wherein the inlet portion is formed on the first surface of the housing such that a biological liquid guided through the inlet portion is guided into the first chamber in a central region of the gas exchanger.

6. The device according to claim 5, wherein the gas exchanger comprises a fiber bundle.

7. The device according to claim 6, wherein in the first chamber and/or the fiber bundle has a substatialy cylindrical shape.

8. The device according to claim 1, further comprising a diaphragm seal adapted to balance a pressure difference in a flow cross-section of the biological liquid, the diaphragm seal being disposed on a side of the first chamber facing the inlet portion.

9. The device according to claim 8, wherein the diaphragm seal defines a oblique plane, the biological liquid being guided along the oblique plane flowing into the device.

10. The device according to claim 1, wherein the first surface and/or the second surface of the housing comprises a cover.

11. The device according to claim 1, further comprising a distributor formed in the device, the distributor adapted to distribute the biological liquid in a direction lateral to a flow direction.

12. The device according to claim 11, wherein the distributor has a side facing the inlet portion, a channel-like portion extending from the inlet-portion-facing side to an opening in the lateral direction to the flow direction of the biological liquid.

13. The device according to claim 11, further comprising a diaphragm seal, the distributor integrally formed with the diaphragm seal and/or the inlet portion and/or a cover and/or the first surface of the housing.

14. The device according to claim 2, further comprising a third chamber disposed in the first chamber and at least one liquid-permeable membrane, the third chamber being separated from the first chamber by the at least one liquid-permeable membrane, the third chamber adapted to extract one or more components of the biological liquid.

15. The device according to claim 12, wherein flow guiding surfaces are defined on both sides of the channel-like portion, the flow guiding surfaces having a slope opposite to a slope of the channel-like portion, so that a first axis defined by the channel-like portion and a second axis defined by the flow guiding surfaces intersect at an acute angle.

16. The device according to claim 15, wherein the acute angle between the first axis and second axis is between 5° and 20°.

* * * * *